United States Patent
Faubert et al.

(10) Patent No.: US 10,706,730 B2
(45) Date of Patent: *Jul. 7, 2020

(54) PERCEPTUAL-COGNITIVE-MOTOR LEARNING SYSTEM AND METHOD

(71) Applicant: COGNISENS INC., Montréal, Québec (CA)

(72) Inventors: Jocelyn Faubert, Montreal (CA); Jean Castonguay, Vaudreuil-Dorion (CA)

(73) Assignee: COGNISENS INC., Montreal, QC (CA)

( * ) Notice: Subject to any disclaimer, the term of this patent is extended or adjusted under 35 U.S.C. 154(b) by 7 days.

This patent is subject to a terminal disclaimer.

(21) Appl. No.: 14/380,407

(22) PCT Filed: Feb. 22, 2013

(86) PCT No.: PCT/CA2013/000166
§ 371 (c)(1),
(2) Date: Aug. 22, 2014

(87) PCT Pub. No.: WO2013/123587
PCT Pub. Date: Aug. 29, 2013

(65) Prior Publication Data
US 2015/0024357 A1   Jan. 22, 2015

Related U.S. Application Data

(60) Provisional application No. 61/601,795, filed on Feb. 22, 2012.

(51) Int. Cl.
*G09B 5/00* (2006.01)
*G09B 23/28* (2006.01)
(Continued)

(52) U.S. Cl.
CPC ............... *G09B 5/00* (2013.01); *G09B 19/00* (2013.01); *G09B 23/28* (2013.01); *A61B 5/1114* (2013.01);
(Continued)

(58) Field of Classification Search
None
See application file for complete search history.

(56) References Cited

U.S. PATENT DOCUMENTS 4,962,420 A * 10/1990 Judenich ................ G03B 21/00
348/218.1
6,164,973 A * 12/2000 Macri ................ G09B 19/0038
345/156
(Continued)

FOREIGN PATENT DOCUMENTS

WO   WO 99/49822         10/1999
WO   WO 2009/046282 A1    4/2009
WO   WO 2010/037222 A1    4/2010

OTHER PUBLICATIONS

Williams, A. M., Ford, P. R., Eccles, D. W., & Ward, P. (2010). Perceptual-cognitive expertise in sport and its acquisition: Implications for applied cognitive psychology. Applied Cognitive Psychology, 25(3), 432-442. doi:10.1002/acp.1710.*
(Continued)

*Primary Examiner* — Jerry-Daryl Fletcher
*Assistant Examiner* — Daniel E Lane
(74) *Attorney, Agent, or Firm* — PRAXIS

(57) ABSTRACT

The present disclosure relates to a perceptual-cognitive-motor learning system. The system includes an apparatus for evaluating or improving perceptual-cognitive abilities of a subject during a training sequence. The system also has a training sequence controller for adding in at least a part of the training sequence at least one of (a) a first motor load add-on to the subject and (b) a second motor load add-on to
(Continued)

the subject, the second motor load being heavier than the first motor load. A variant of the system has a user interface for allowing the subject to change at least one parameter of the training sequence. Methods for evaluating or improving perceptual-cognitive abilities of a subject are also disclosed.

15 Claims, 6 Drawing Sheets

(51) Int. Cl.
  *G09B 19/00* (2006.01)
  *A61B 5/11* (2006.01)
(52) U.S. Cl.
  CPC ....... *A61B 2503/10* (2013.01); *A61B 2505/09* (2013.01)

(56) References Cited

U.S. PATENT DOCUMENTS

| | | | |
|---|---|---|---|
| 6,234,979 B1 | 5/2001 | Merzenich | |
| 6,271,808 B1* | 8/2001 | Corbin | G02B 27/0172 345/7 |
| 6,425,764 B1* | 7/2002 | Lamson | A61M 21/00 434/236 |
| 6,437,777 B1* | 8/2002 | Kamachi | G06F 3/04815 345/419 |
| 6,632,174 B1* | 10/2003 | Breznitz | A61B 5/16 600/300 |
| 6,896,655 B2* | 5/2005 | Patton | A61M 21/00 351/240 |
| 8,016,416 B1* | 9/2011 | Straus | A61B 5/1171 351/200 |
| 8,090,488 B2 | 1/2012 | Agrawal et al. | |
| 8,154,473 B2* | 4/2012 | Engel | G09G 3/36 345/4 |
| 10,096,258 B2* | 10/2018 | Faubert | G09B 19/0038 |
| 2003/0013981 A1* | 1/2003 | Gevins | A61B 5/0484 600/544 |
| 2003/0059759 A1* | 3/2003 | Calhoun | A61B 5/16 434/322 |
| 2003/0077556 A1* | 4/2003 | French | A61B 5/1113 434/258 |
| 2004/0002046 A1* | 1/2004 | Cantor | A61B 5/18 434/322 |
| 2004/0049124 A1* | 3/2004 | Kullok | A61B 5/16 600/558 |
| 2004/0230549 A1* | 11/2004 | Freer | A61B 5/0482 706/61 |
| 2005/0216243 A1* | 9/2005 | Graham | G16H 50/50 703/11 |
| 2005/0270367 A1* | 12/2005 | McDowall | G02B 27/0093 348/51 |
| 2006/0003298 A1* | 1/2006 | Greenshpan | A63B 24/0003 434/247 |
| 2007/0004513 A1* | 1/2007 | Wells | G07F 17/3202 463/31 |
| 2007/0005540 A1 | 1/2007 | Fadde | |
| 2007/0048702 A1* | 3/2007 | Jang | G09B 19/00 434/224 |
| 2007/0166675 A1* | 7/2007 | Atkins | G09B 5/06 434/236 |
| 2007/0196809 A1* | 8/2007 | Sen | A63F 13/02 434/365 |
| 2007/0218440 A1* | 9/2007 | Delahunt | G09B 7/02 434/236 |
| 2007/0293735 A1* | 12/2007 | Chan | A61B 5/16 600/300 |
| 2008/0161080 A1* | 7/2008 | Terasaki | A63F 13/10 463/9 |
| 2008/0280276 A1* | 11/2008 | Raber | A61B 5/16 434/236 |
| 2009/0046140 A1* | 2/2009 | Lashmet | G09G 3/002 348/51 |
| 2009/0111073 A1* | 4/2009 | Stanley | F41A 33/00 434/21 |
| 2009/0295683 A1* | 12/2009 | Pugh | G02B 27/0101 345/9 |
| 2010/0255449 A1* | 10/2010 | Fadde | A63B 24/0006 434/236 |
| 2011/0007275 A1* | 1/2011 | Yoo | A61B 3/113 351/209 |
| 2011/0213197 A1* | 9/2011 | Robertson | G16H 50/50 600/27 |
| 2011/0298706 A1* | 12/2011 | Mann | G06F 3/015 345/157 |
| 2011/0300522 A1* | 12/2011 | Faubert | G09B 9/00 434/236 |
| 2012/0090446 A1* | 4/2012 | Moreno | G09B 15/00 84/470 R |
| 2013/0046206 A1* | 2/2013 | Preminger | G09B 7/02 600/595 |
| 2013/0266918 A1* | 10/2013 | Tinjust | A63B 69/0053 434/247 |
| 2016/0155355 A1* | 6/2016 | Merzenich | A63F 13/80 434/236 |

OTHER PUBLICATIONS

Jocelyn Faubert, et al., "Perceptual-Cognitive Training of Athletes," Journal of Clinical Sport Psychology, 2012, 6, 85-102.
I-Perception, "Healthy older observers cannot use biological-motion point-light information efficiently within 4 m of themselves," 2012, vol. 3, pp. 1-8, ISSN 2041-6695, perceptionweb.com/i-perception.

* cited by examiner

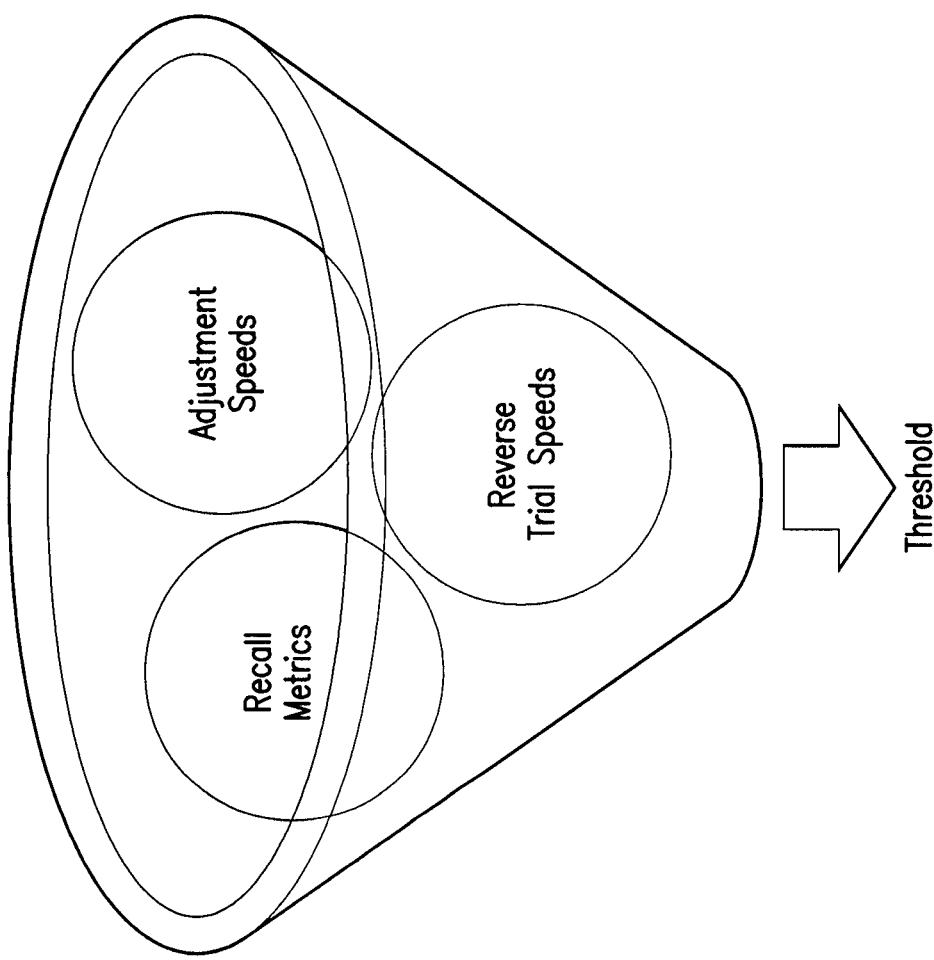

PERCEPTUAL-COGNITIVE-MOTOR LEARNING SYSTEM AND METHOD

TECHNICAL FIELD

The present disclosure relates to the field of perceptual-cognitive training. More specifically, the present disclosure relates to a perceptual-cognitive-motor learning system and method.

BACKGROUND

In our daily activities, we constantly interact with our environment. This environment is dynamic and requires the integration of various objects, motions, speeds, locations, etc. As a result, the brain's executive functions are constantly managing myriads of stimuli. Risk of information overload is present in many real-life situations. Ability to deal quickly with unpredictability of stimuli in time sensitive situations is a real-life need in the office, in sports, in school, and in crisis management situations.

Attention and focus applied to strategic inputs can make a difference between winning and losing in sports activities, in learning new skills, in facing dangerous situations, and leading a successful professional career. Attention and focus, especially in stressful situations, enable filtering and prioritizing of data while disregarding irrelevant distractors.

In the case of elderly people or persons with certain disabilities, deficits in attention and focus can cause serious problems in routine activities. For instance, travelling through a crowd while avoiding collisions and maintaining orientation and good motor control requires fluent and continuous perceptual-cognitive processing. It is well documented that effects of healthy aging can influence perceptual cognitive processes.

Loss of attention and impaired impulse control can be a severe problem for children with attention deficit disorder, with or without hyperactivity, and for autistic children.

The need to improve attention and focus is therefore present in a broad range of individuals. This need is especially present in persons having learning disabilities or with degrading cognitive functions. This need is also present in elite athletes who need to "read the game" while following the trajectory of a ball, and in members of many professions who need deal with masses of information.

Therefore, there is a need for solutions that help improve cognitive functions, whether for children having learning disabilities, aging persons, athletes or professionals operating in stressful environments.

SUMMARY

According to the present disclosure, there is provided a perceptual-cognitive-motor learning system. The system comprises an apparatus for evaluating or improving perceptual-cognitive abilities of a subject during successive tests. The system also comprises at least one of (a) means for adding in at least a part of the tests a low-level motor load add-on to the subject causing no efferent signal from the subject's brain and (b) means for merging in at least one of the tests a specific motor demand to the subject that is adapted to a given real-life situation.

According to the present disclosure, there is also provided a perceptual-cognitive-motor learning system. The system comprises an apparatus for evaluating or improving perceptual-cognitive abilities of a subject during a training sequence. The system also comprises a training sequence controller for adding in at least a part of the training sequence at least one of (a) a first motor load add-on to the subject and (b) a second motor load add-on to the subject, the second motor load being heavier than the first motor load.

According to the present disclosure, there is also provided a perceptual-cognitive-motor learning system. The system comprises an apparatus for evaluating or improving perceptual-cognitive abilities of a subject during successive tests. The system also comprises means for allowing the subject to change at least one parameter of the tests performed by means of the apparatus.

The present disclosure also relates to a perceptual-cognitive-motor learning system. The system comprises an apparatus for evaluating or improving perceptual-cognitive abilities of a subject during a training sequence. The system also comprises a user interface for allowing the subject to change at least one parameter of the training sequence.

The present disclosure further relates to a method for evaluating or improving perceptual-cognitive abilities of a subject. The subject is submitted to a training sequence. At least one of (a) a first motor load add-on to the subject and (b) a second motor load add-on to the subject is added in at least a part of the training sequence, the second motor load being heavier than the first motor load.

The present disclosure also relates to a method for evaluating or improving perceptual-cognitive abilities of a subject. The subject is submitted to a training sequence. A command to change at least one parameter of the training sequence is received from the subject.

The foregoing and other features will become more apparent upon reading of the following non-restrictive description of illustrative embodiments thereof, given by way of example only with reference to the accompanying drawings.

BRIEF DESCRIPTION OF THE DRAWINGS

Embodiments of the disclosure will be described by way of example only with reference to the accompanying drawings, in which:

FIG. 6 is a schematic diagram illustrating the use of a number of measures to determine speed thresholds.

DETAILED DESCRIPTION

Like numerals represent like features on the various drawings.

Various aspects of the present disclosure generally address one or more of the problems of improving cognitive functions.

The following description discloses the NeuroTracker "Perceptual-Cognitive-Motor" Learning System (NT-LS). More specifically, the two (2) following features of the NT-LS are described:

1—A NeuroTracker (NT) motor add-on system where motor add-ons are made under very specific conditions for optimized learning.

2—A "SelfPaced" system and method for rapidly assessing individual thresholds.

1—The NT-Motor Add-On System

Sports performance (also true for common life situations like navigation in crowds) involves the capacity to rapidly process complex movement over large areas and in a three-dimensional (3D) environment, including sudden changes in directions and collisions and at the same time attend to multiple key elements in the scene, i.e. in the environment. Information from the scene is integrated with specific motor demands in the sport or for real-life demands like navigating in crowds. In other words, human beings perceive and understand what is happening in their environment while at the same time interacting with it physically, with specific actions. There is evidence for specialized visual brain systems where some pathways are responsible for perception and some for action. Although these specialized visual brain systems for perception and for action comprise distinctive elements they are ultimately combined.

It is also believed with evidence from science that the vision for perception system is more complex and more recent on the evolutionary scale than the vision for action system.

The ultimate transfer and closure of the sensory-perceptual-cognitive-motor loop involves a way to combine all of the above abilities in training. It is also desirable to isolate and consolidate these abilities and then combine them on training. The present disclosure proposes to train on the NT-LS to build this consolidation, as it involves the more complex visual system and, once consolidated, close the visual-perceptual-cognitive-motor loop with motor tasks integrated with the NT.

1a)—Evidence for Requiring the Consolidation Process

Figure 1:
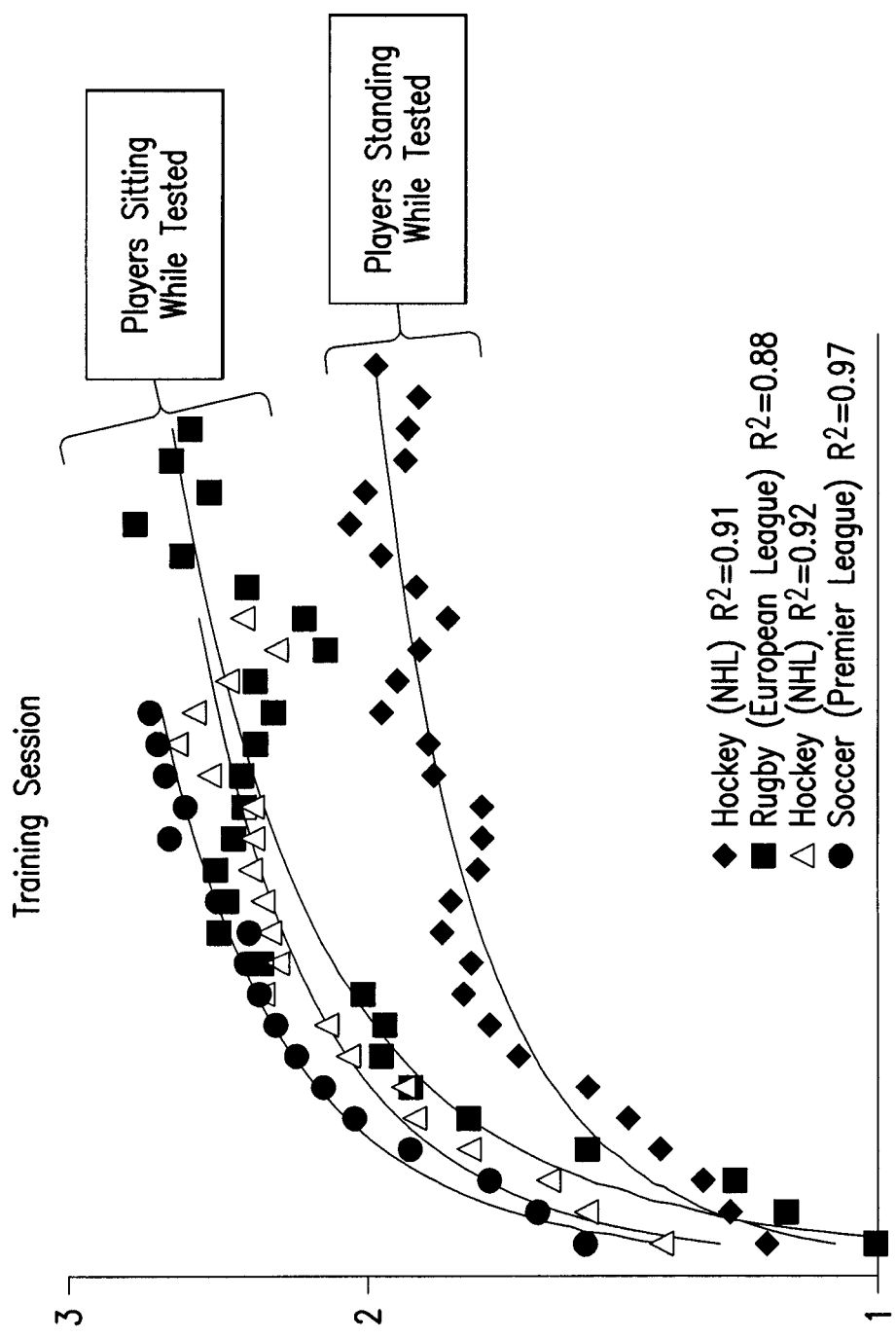
FIG. 1 is a graph showing learning curves of athletes subjected to a demanding training regime.
Figure 2:
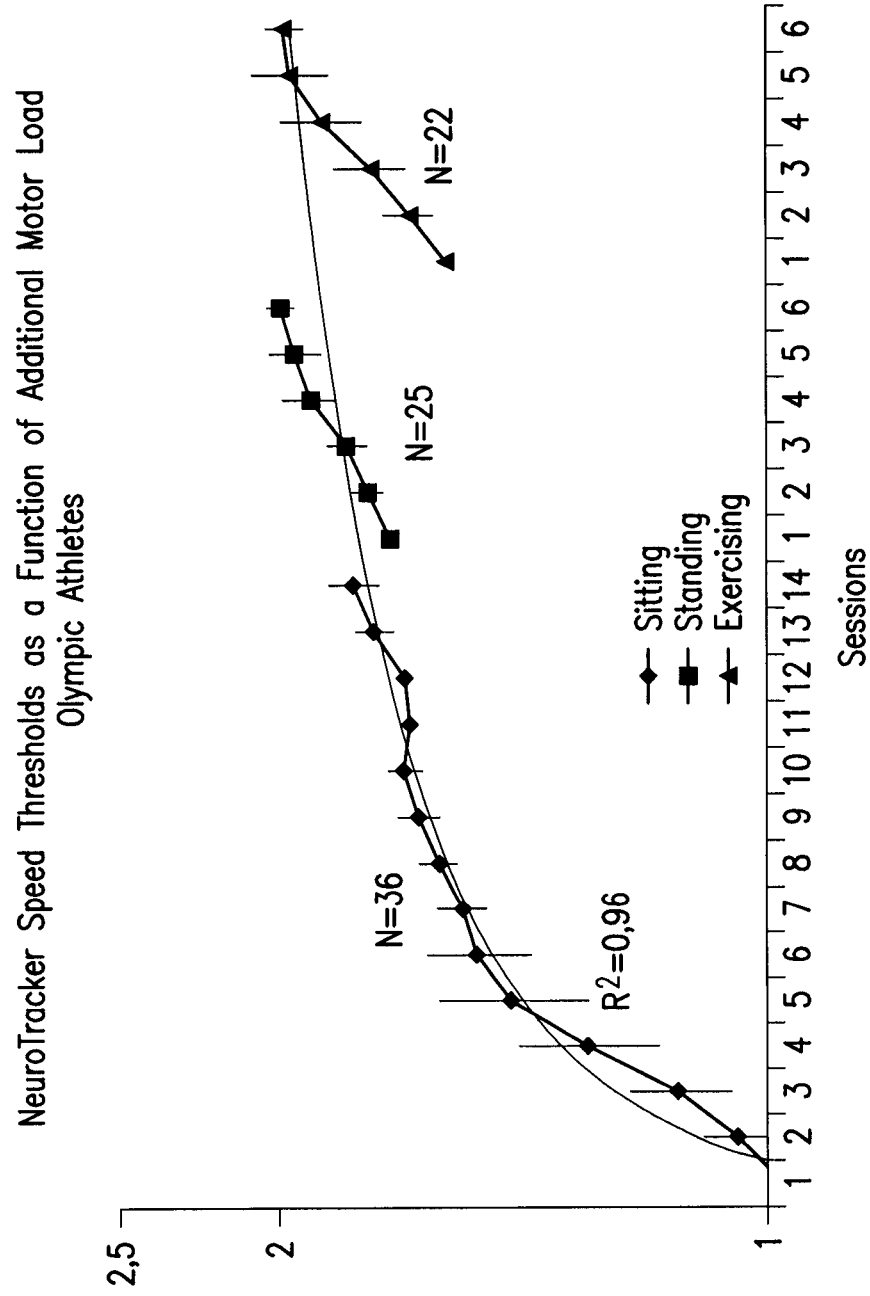
FIG. 2 is a graph showing learning curves of athletes subjected to a demanding training regime when using a perceptual-cognitive-motor system.

An initial study has demonstrated that added motor demand at the beginning of a demanding perceptual-cognitive training regime can be detrimental to the acquisition phase. FIG. 1 is a graph showing learning curves of athletes subjected to a demanding training regime. The graph demonstrates that added motor demand at the beginning of a demanding perceptual-cognitive training regime can be detrimental to a subject's acquisition phase. What was found from training of high-level professional athletes was that if the players learned a task standing up from start, their levels of performance were lower and their learning curves were shallower. To understand this further, the initial study was followed with an experiment looking at the transferability of training when carrying out consolidation first followed by adding motor load on top of the training. What it is meant by transferability is that the benefit of learning in one condition is maintained in another condition. The results of this study are shown in FIG. 2, which is a graph showing learning curves of athletes subjected to a demanding training regime when using a perceptual-cognitive-motor system. This graph shows that, following consolidation when the subject is sitting, very little loss in performance is observed when standing, and that although there is an initial large drop in a condition of exercising, athletes quickly regain their speed processing capacities and get back on the usual learning curve of the "sitting down" position. The first 14 training sessions show the usual progression of speed of processing ability when sitting down, followed by the next six sessions with the athlete standing up, followed by the last six training sessions with the athlete sitting on a Bosu™ balance ball in a position that makes it difficult to maintain balance. As can be observed from FIG. 2, after consolidation (sitting), there is very little loss in performance when standing, which shows evidence of transfer. Although there is an initial large drop in the third condition (exercising; sitting on Bosu™ ball) the athletes quickly regain their speed processing capacities and get back on the usual learning curve of the "sitting down" position.

1b)—Closing the Loop

This section describes a method and system for closing of the visual-perceptual-cognitive-motor loop for optimal performance and combining of the NT technology with an objective measure of visual-motor performance system. A subject is submitted to a training sequence according to the following scheme:

[$n_1$(CORE);$n_2$(CORE+MOTORa);$n_3$(CORE+MOTORb)].

The training sequence comprises $n_1$ repetitions of a core exercise, followed by $n_2$ repetitions of the core exercise performed in conjunction with a first (usually light) motor demand, and followed by $n_3$ repetitions of the core exercise performed in conjunction with a second (usually heavier) motor demand. Generally, the values of $n_1$, $n_2$ and $n_3$ are non-negative integers.

As a non-limitative example, the training can be performed using an apparatus as described in PCT patent application No PCT/CA2009/001379 filed on Sep. 29, 2009 in the name of Faubert et al., and published on Apr. 8, 2010 under No WO 2010/037222 A1 (hereinafter "Faubert'222"), the full content of which being herein incorporated by reference.

Figure 3:
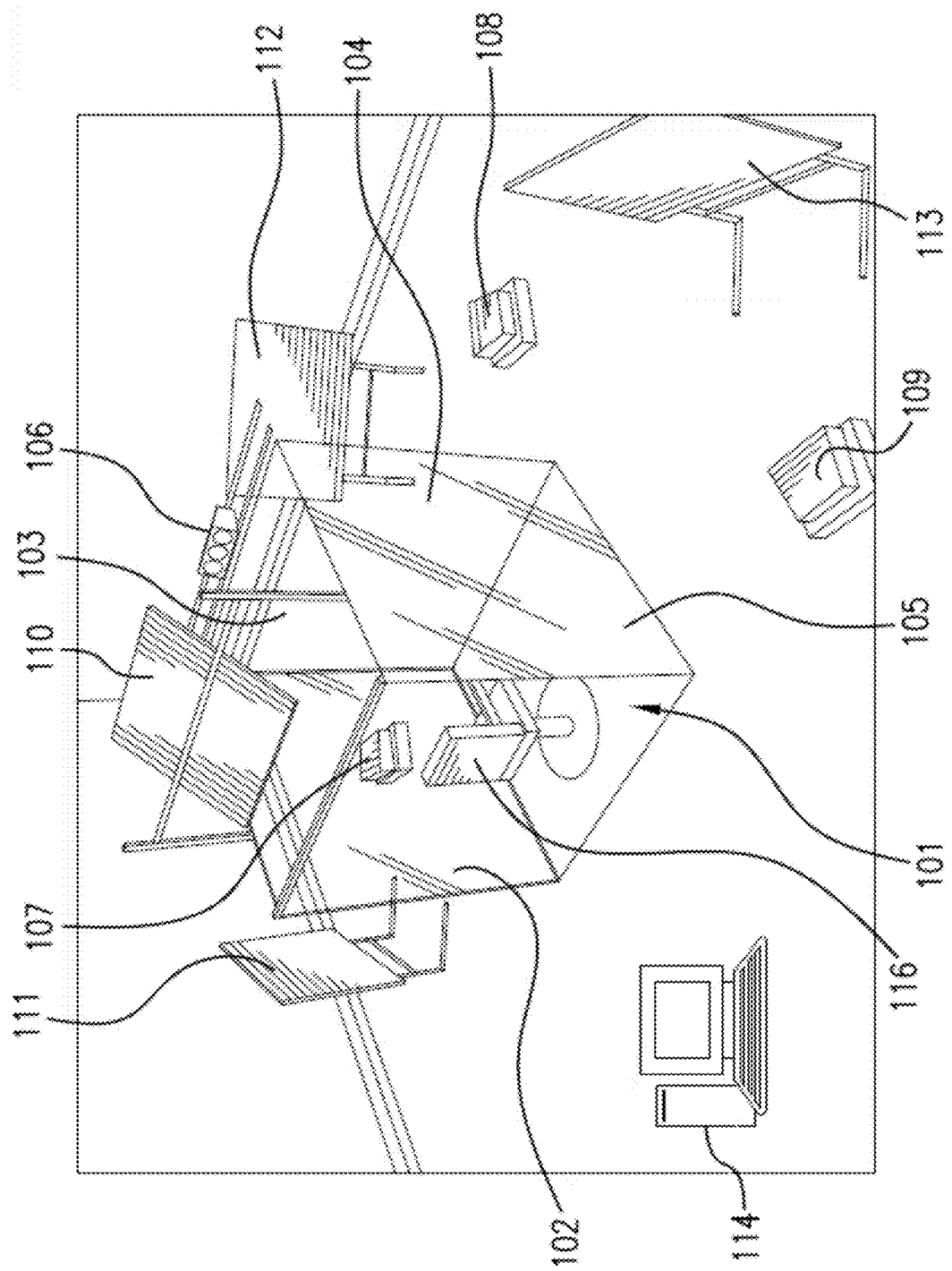
FIG. 3 (Prior art) is a perspective view of an example of full immersive virtual environment.

The apparatus introduced in Faubert'222 can be used for evaluating or improving perceptual-cognitive abilities of a subject. The apparatus comprises a display of virtual objects moving a given 3D environment during successive tests. FIG. 3 is a perspective view of an example of full immersive virtual environment. More specifically, the display comprises a fully immersive virtual environment (FIVE) room 101, for example a CAVE™ Automatic Virtual Environment, from Fakespace Systems, in which the subject is fully immersed in the given 3D environment and the stimuli are presented. The fully immersive virtual environment room 101 has a size of, for example, 8×8×8 feet and comprises four (4) projection surfaces (three walls 102, 103 and 104 and a floor 105). The display shows stereoscopic images on the four (4) projection surfaces (the three walls 102, 103 and 104 and floor 105) to form the given 3D environment in which virtual objects are presented. The display comprises, for that purpose, projectors 106, 107, 108 and 109 and associated planar reflectors 110, 111, 112 and 113, respectively to project and display the images on the four (4) projection surfaces (the three walls 102, 103 and 104 and floor 105) under the control of a computer 114 acting as a display controller. Interconnections between the computer 114 and other elements of the FIVE room 101 are not shown for simplicity purposes. The computer 114 may be linked to the various projectors 106, 107, 108 and 109 and to other networked elements using any well-known connection methods.

The display of the apparatus for evaluating or improving perceptual-cognitive abilities of a subject also comprises a shutter visual implement, for example under the form of liquid crystal shutter stereoscopic goggles (not shown) from Stereographics, San Rafael, Calif., to enable the subject's 3D stereoscopic perception, more particularly to enable the subject to perceive in 3D the virtual object, the positions of the virtual objects and the 3D environment. Stereoscopic images are rendered with a refresh rate of 48 Hz and the goggles are shuttered at 96 Hz to deliver 48 images per second to the subject's right and left eyes. The display further comprises a positional sensor, for example under the form of a magnetic detector, for example a Flock of Birds™, from Ascension technology corp., Burlington, Vt., mounted to the goggles in order to track a position of the subject's head. The computer 114 controls the display to correct in real-time a visual perspective relative to the tracked subject's head position. The display controller (for example a "Silicon graphics 540" computer) generates the stimuli and records the subject's responses.

An ophthalmologic chair 116 positioned substantially in a central position of the FIVE room 101 is provided to sit the subject.

The apparatus of Faubert '222 can therefore be used in support of a method for evaluating or improving perceptual-cognitive abilities of a subject. In summary, this apparatus comprises a display of virtual objects moving in a given 3D environment during successive tests, with the subject in visual contact with the virtual objects moving in the 3D environment. The computer 114 controls the projectors 106, 107, 108 and 109 to change a speed of movement of the virtual objects in the 3D environment. During each test, the subject tracks a subset of the moving virtual objects and, after the test, the subject identifies the tracked objects. It should be kept in mind that the training can be performed using any other suitable device.

The core exercise may include, as a non-limitative example, placing the subject in visual contact with the virtual objects, for example spheres, moving within a pair of virtual transparent planes displayed in the 3D environment. A training sequence controller, integrated in the computer 114 or in a separate computer (not shown), controls the display to execute, during each test, the following sequence of phases:

Presentation phase: A number of spheres, for example six (6) yellow spheres may be presented to the subject in each plane for 2.5 seconds, in random positions, and with a spatial restriction of 2 centimetres between the spheres.

Indexation phase: A number of spheres, for example two (2) spheres in each plane may turn red for 2 seconds to be identified as target spheres by the subject. Then, these two (2) spheres return to their initial colour (yellow).

Tracking phase: All the spheres move for 6 seconds while the target spheres are tracked by the subject. After the duration of 6 seconds, the movement of the spheres is stopped. During the period of 6 seconds, the spheres embedded in each virtual transparent plane are enabled to collide with each other and the edges of the virtual transparent plane.

Response phase: In this phase, each sphere is associated to a number from 1 to 12, and the subject verbally identifies, as response to the test, the spheres formerly identified as target spheres.

Feedback phase: Following the response phase, the four (4) spheres actually identified as target spheres turn red for 3 seconds to give feedback to the subject.

CORE represents a test comprising a 6-8 minutes testing sequence using the apparatus as described in Faubert'222.

CORE+MOTORa represents a test comprising a low-level simple motor load add-on to the CORE test. This can be a standing up position but could also be holding onto a rail or a treadmill with ice skates or roller skates. This means that the CORE+MOTORa test is calibrated so that there is no conscious efferent signal (brain command of movement) from the brain to move limbs in a meaningful pattern such as running, skating or intercepting a ball.

CORE+MOTORb represents a test going one level higher, the MOTORb load thus being heavier than the MOTORa load. During a CORE+MOTORb test, the subject is asked to merge the CORE with a specific motor demand that is adapted to a given real-life situation, for example a sport, operation of a machine or of a vehicle, a hazardous situation, or any other similar purpose. Non-limiting examples of MOTORb add-ons include a motor task such as a catch or an interception in response to a simulated stimulus such as a ball thrown for a pass, bouncing of a soccer ball, stopping of a puck, and the like. Other non-limiting examples of added MOTORb elements include an involuntary response, either physical or emotional (or both), to a potentially threatening simulated visual stimulus such as an unpredicted target with a trajectory potentially colliding with the face or other sensitive parts of the subject's body, the visual stimulus possibly being accompanied with a sound. There is no a priori limit to the type of situation that can be represented during the CORE+MOTORb test.

A training sequence controller, integrated in the computer 114 or in a separate computer (not shown), controls the apparatus as described in Faubert'222 in order to perform the training sequence. Sensors may also be connected to the training sequence controller for monitoring the movements of the subject during each test, in particular movements related to MOTORa add-ons and MOTORb movement.

According to an example of implementation taking into consideration available gathered scientific data, the following training sequence is performed under the control of the training sequence controller:

$$[n_1(CORE);n_2(CORE+MOTORa);n_3(CORE+MOTORb)].$$

wherein:

$n_1$=10 to 15 repetitions;

$n_3$=6 repetitions; and $n_3$=6 repetitions.

More specifically, the training sequence controller controls the apparatus as described in Faubert'222 to perform, in sequence, a series of 10 to 15 CORE tests, a series of 6 CORE+MOTORa tests, and a series of 6 CORE+MOTORb tests. After each test, the computer 114 collects the responses of the subject in relation to the identification of the tracked balls through a response interface, for example a keyboard with a display of the computer 114, for further analysis of these responses, for example an analysis as described in the aforementioned Faubert'222, potentially in combination with an analysis of the movements of the subject during the tests in case of CORE+MOTORa and CORE+MOTORb tests to determine the evolution of the subject. Such analysis of the training sequence can be limited to the tracing of graphs or can be much more complex depending on the requirements of the intended application.

Using the above example of implementation ($n_1$=10 to 15 repetitions, $n_3$=6 repetitions, and $n_3$=6 repetitions), it is possible to increase motor skill with a method based on scientific data and adapt it to any sport or rehabilitation training. For instance, it is easy to imagine someone who suffered a stroke and had some difficulty walking, to be gradually rehabilitated using such a method where MOTORb becomes walking on a treadmill. The following are also some examples of MOTORb:

Rugby: Catching a lateral pass;

Hockey: Receiving a pass and shooting puck, or stopping a puck for a goalie;

Soccer: receiving an redirecting a ball;
Etc.

2) "Self-Paced" System and Method

The self-paced system and method address some issues by the users (subjects) of the NT-LS system. These issues comprise:

A technique for getting speed thresholds more rapidly than the usual 6-8 minutes CORE test in situations such as testing at combines (recruitment of junior drafts), rapid throughput, etc.

A technique to keep the subject active during the test even if the subject lost tracking of the virtual objects (see the apparatus as described in Faubert'222). The classic CORE test is set-up so that if the subject loses one or more of the tracked objects, there was no chance of reset or recall during the test that lasts 6-8 seconds. The subject waits until the end, gives the response and starts again.

The self-paced system and method resolves this issue by allowing the subject to stay active and do several things on his own and online to the dynamic visual scene. Also, there are two versions of the self-paced system and method, the training mode and the assessment (measurement) mode although these two versions are not mutually exclusive.

Figure 4:
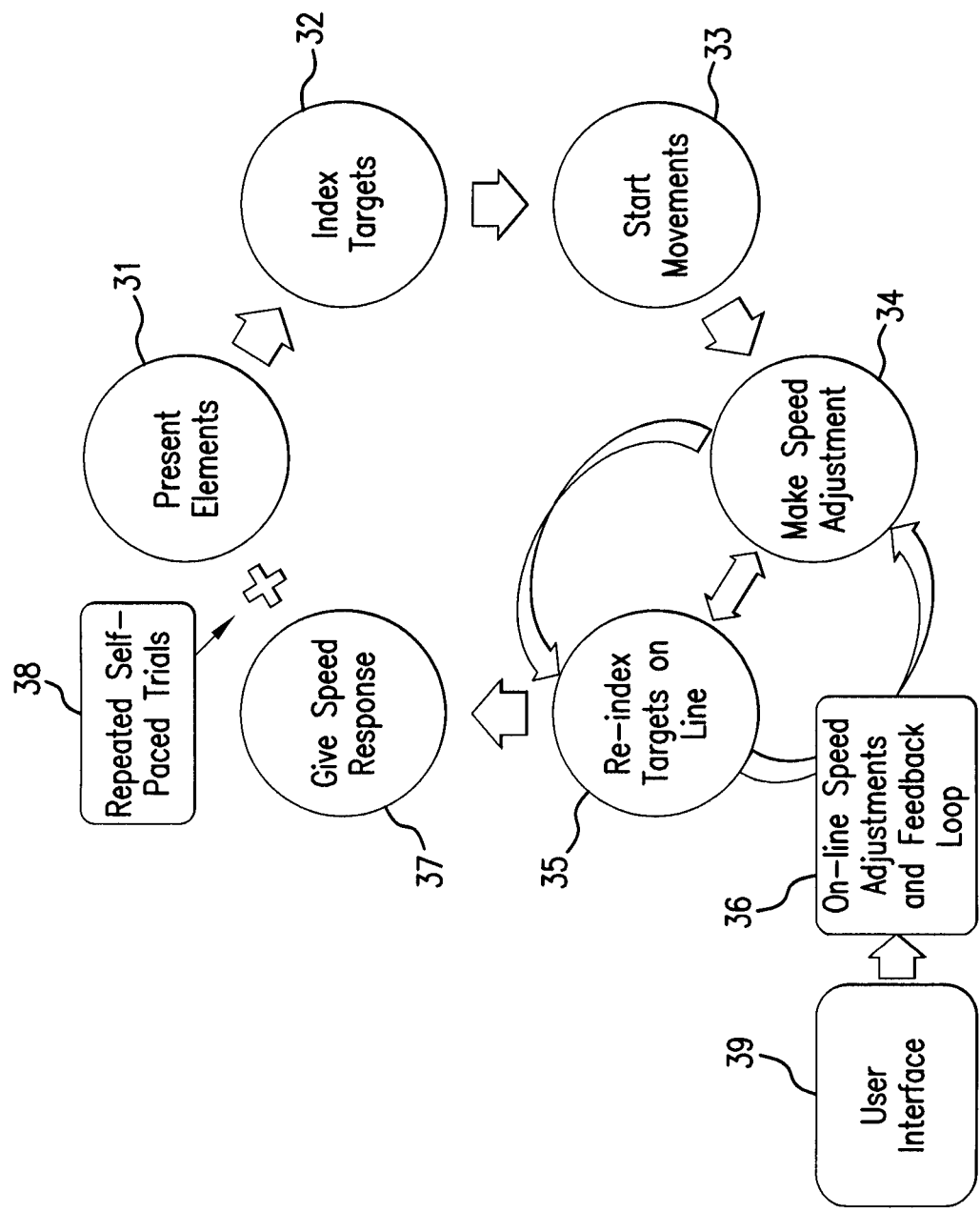
FIG. 4 is a schematic diagram illustrating a training self-paced mode.

Referring to FIG. 4, which is a schematic diagram illustrating a training self-paced mode, a typical CORE test works the following way. As directed by the training sequence controller, the display of the apparatus as described in Faubert'222 presents to the subject a number of virtual objects (typically 8 spheres) as seen in block 31 of FIG. 4. Then the training sequence controller indexes a subset (usually 4 spheres representing the target objects) by changing color or flashing, etc. (block 32 in FIG. 4). Then the objects return to their original condition. The training sequence controller then starts movement of the objects in the 3D environment as shown in block 33 of FIG. 4. Once the movement of the objects starts then the subject can use a user interface 39, which is operatively connected to the computer 114, to make the following adjustments:

Training self-paced mode: In this case the subject can issue commands directed to the training sequence controller via the user interface 39 to perform the following actions:

Managing the speed, i.e. make the virtual objects in the dynamic 3D environment move faster or slower at will by pressing buttons or giving certain commands, for example vocal commands to a remote module (not shown). The remote module or motion capture device is connected to the computer 114 that incorporates the training sequence controller (blocks 34 and 36 of FIG. 4).

Allowing for a reset, recall or re-indexing of the target objects at any time during tracking and for any desired length up to a certain limit (block 35 of FIG. 4).

At any time during the test, the subject can indicate by depressing a button of the remote module or through any other command, that a given speed of the virtual objects is the correct tracking speed (block 37 of FIG. 4). More specifically, when the subject feels the speed is correct and he can maintain the tracking of the target objects at that speed, the subject then presses a button of the remote module and the selected speed is automatically received and recorded by the computer 114. When this is done, the test is refreshed and a new set of target objects is presented and the test is started again. This can be repeated any number of times (block 38 of FIG. 4). That is, one subject can train for as long as desired by providing feedback commands to the self-paced system. The subject can continue using the method without resetting or may have as many rests as desired.

Depending on the type of adjustment made by the subject in the training self-pace mode, the user interface 39 may comprise one or more buttons, a microphone connected to a speech detector (not shown), a keyboard or a pedal board.

Figure 5:
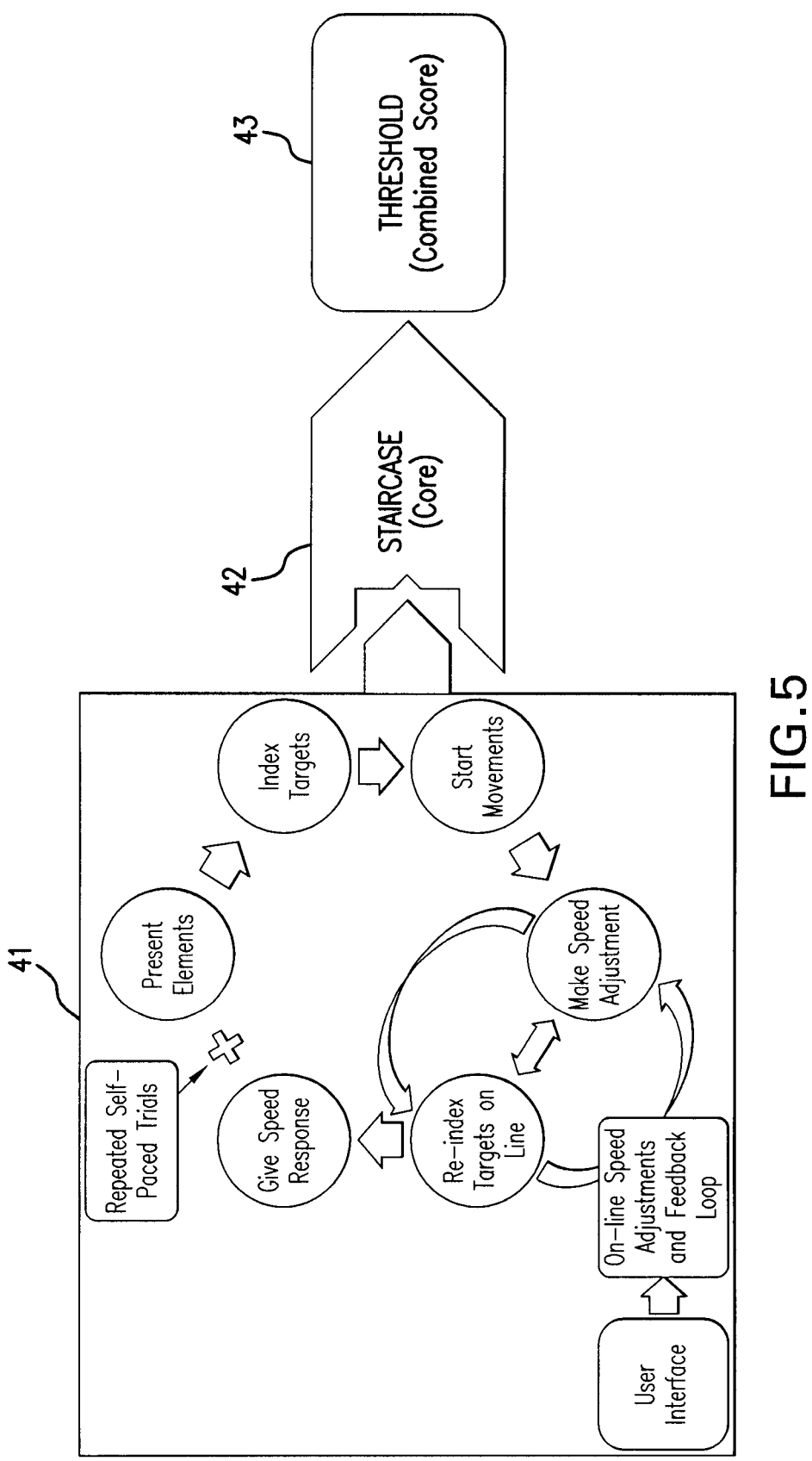
FIG. 5 is a schematic diagram illustrating an assessment self-paced mode incorporating the training self-paced mode of FIG. 4 and an additional use of a staircase (up and down) variation of speeds.

Assessment self-paced mode: FIG. 5 is a schematic diagram illustrating an assessment self-paced mode incorporating the training self-paced mode of FIG. 4 and an additional use of a staircase (up and down) variation of speeds. The assessment self-paced mode incorporates the operations of the training self-paced mode (block 41 of FIG. 5) except that it has the following additional step (block 42 of FIG. 5):

When a pre-set number of speed adjustments has been terminated in block 41, the training sequence controller automatically performs a preset number of tests using a shortened staircase (up and down) variation of speeds such as the one used for the CORE test and as described in the apparatus of Faubert'222. This procedure ensures that the subjective speed adjustments made by the subject truly correspond to speed threshold values as objectively determined (block 42 of FIG. 5).

The "self-paced" system and method have the following characteristics:

1) They can be very fast;
2) They are very flexible for various training times;
3) They permit the subject to stay in the "zone" of maximum trainability where stands the right level of difficulty for any subject at any given time; and
4) It develops the subject's ability to recognize their own internal mental state and respond to it by making appropriate adjustments.

The self-paced system and method not only assess speed thresholds (block 43 of FIG. 5) by calculating the given responses and the results of the staircase variation of speed (block 42 of FIG. 5) when the assessment self-paced mode is used, but it also allows the computer 114 to perform a number of measures, useful in determining the speed thresholds, while the subject is participating such as:

a) A number of test recalls (number of repetitions of the self-paced trials);
b) A time of each recall (repetition rate of the self-paced trials); and
c) Speed values during the self-paced trials.

This is illustrated in FIG. 6, which is a schematic diagram illustrating the use of a number of measures to determine speed thresholds, and can be used to develop response profiles and learning profiles for each subject.

The efficiency of the self-paced assessment mode to determine whether this mode can generate similar results as the CORE test for the initial "consolidation" stage has been tested. During the test, the subjects used the assessment self-paced mode (2 adjustments and 6 staircase trials) for the first 4 training sessions, followed by a regular CORE assessment measure on the 5th session followed by another 4 assessment self-paced sessions followed by a CORE session as the 10th session etc. It was found that the 5th, 10th and 15th CORE session scores followed well with the self-paced score indicating that the assessment self-paced mode can be used to obtain similar results but with much shorter training times i.e. 3 minutes versus 6-8 minutes with the CORE test.

Those of ordinary skill in the art will realize that the description of the perceptual-cognitive-motor system and method are illustrative only and are not intended to be in any way limiting. Other embodiments will readily suggest themselves to such persons with ordinary skill in the art having the benefit of the present disclosure. Furthermore, the disclosed perceptual-cognitive-motor system and method may be customized to offer valuable solutions to existing needs and problems of improving cognitive functions.

In the interest of clarity, not all of the routine features of the implementations of the perceptual-cognitive-motor system and method are shown and described. It will, of course, be appreciated that in the development of any such actual implementation of the perceptual-cognitive-motor system and method, numerous implementation-specific decisions may need to be made in order to achieve the developer's specific goals, such as compliance with application-, system-, and business-related constraints, and that these specific goals will vary from one implementation to another and from one developer to another. Moreover, it will be appreciated that a development effort might be complex and time-consuming, but would nevertheless be a routine undertaking of engineering for those of ordinary skill in the field of perceptual-cognitive training having the benefit of the present disclosure.

In accordance with the present disclosure, the components, process steps, and/or data structures described herein may be implemented using various types of operating systems, computing platforms, network devices, computer programs, and/or general purpose machines. In addition, those of ordinary skill in the art will recognize that devices of a less general purpose nature, such as hardwired devices, field programmable gate arrays (FPGAs), application specific integrated circuits (ASICs), or the like, may also be used. Where a method comprising a series of process steps is implemented by a computer or a machine and those process steps may be stored as a series of instructions readable by the machine, they may be stored on a tangible medium.

Systems and modules described herein may comprise software, firmware, hardware, or any combination(s) of software, firmware, or hardware suitable for the purposes described herein. Software and other modules may reside on servers, workstations, personal computers, computerized tablets, personal digital assistants (PDA), and other devices suitable for the purposes described herein. Software and other modules may be accessible via local memory, via a network, via a browser or other application or via other means suitable for the purposes described herein. Data structures described herein may comprise computer files, variables, programming arrays, programming structures, or any electronic information storage schemes or methods, or any combinations thereof, suitable for the purposes described herein.

Although the present disclosure has been described hereinabove by way of non-restrictive, illustrative embodiments thereof, these embodiments may be modified at will within the scope of the appended claims without departing from the spirit and nature of the present disclosure.

What is claimed is:

1. A perceptual-cognitive-motor learning system, comprising:
   an apparatus for improving perceptual-cognitive abilities of a subject during a plurality of successive tests, the apparatus including:
   a three-dimensional display apparatus configured to display stereoscopic images of virtual objects moving in a given three-dimensional environment during the plurality of successive tests, the display apparatus providing a visual contact between the virtual objects and a subject during the plurality of successive tests;
   a user interface for providing commands issued by the subject to a training sequence controller,
   the training sequence controller being operatively connected to the user interface for receiving the commands issued by the subject and to the three-dimensional display apparatus, the training sequence controller being configured to:
      define a training sequence, the training sequence including a first plurality of successive tests, a second plurality of successive tests having a first motor load causing no efferent signal from the subject's brain and a third plurality of successive tests having a second motor load, the second motor load being heavier than the first motor load, wherein the virtual objects move in the three-dimensional environment during the first, second and third plurality of successive tests;
      cause the display apparatus to present the virtual objects in accordance with the first plurality of successive tests to the subject;
      receive, through the user interface, responses from the subject, the responses identifying the virtual objects during the first plurality of successive tests;
      receive, through the user interface, commands from the subject, the commands causing the training sequence controller to perform at least one of:
         causing the display apparatus to change a movement speed of the virtual objects;
         causing the display apparatus to reset the movement of the virtual objects; and
         setting a tracking speed of the virtual objects and presenting again the first plurality of successive tests to the subject, the movement speed of the virtual objects corresponding to the tracking speed;
      cause the display apparatus to present the virtual objects in accordance with the second plurality of successive tests to the subject;
      receive, through the user interface, responses from the subject, the responses identifying the virtual objects during the second plurality of successive tests;
      cause the display apparatus to present the virtual objects in accordance with the third plurality of successive tests to the subject;
      receive, through the user interface, responses from the subject, the responses identifying the virtual objects during the third plurality of successive tests;
      adjust the movement speed of the virtual objects in view of the responses received from the subject.

2. A system as defined in claim 1, wherein each test of the training sequence includes a core exercise.

3. A system as defined in claim 1, wherein the second motor load is a specific motor demand adapted to a given real-life situation.

4. A system as defined in claim 1, wherein the second motor load is selected from a motor task, a visual stimulus, a visual stimulus accompanied by a sound, and a combination thereof.

5. A system as defined in claim 1, further comprising one or more sensors operatively connected to the training sequence controller for monitoring movements of the subject.

6. A system as defined in claim 1, wherein tests in the training sequence comprise tracking the virtual objects in the three-dimensional environment.

7. A system as defined in claim 1, wherein the training sequence controller is further configured to change the movement speed of the virtual objects in accordance with a staircase variation of speed.

8. A system as defined in claim 7, wherein the training sequence controller is further configured to determine a speed threshold based on responses from the subject to the staircase variation of speed of movement of the virtual objects.

9. A system as defined in claim 1, wherein the training sequence controller is further configured to automatically perform a preset number of tests using a shortened staircase variation of speed of the virtual objects after a pre-determined number of speed adjustments by the subject.

10. A system as defined in claim 1, further comprising a shutter visual implement to be worn by the subject, the shutter visual implement having mounted thereon a positional sensor to track a position of the subject's head.

11. A system as defined in claim 1, wherein the user interface is selected from a group consisting of one or more buttons, a microphone, a motion capture device, a keyboard and a pedal board.

12. A perceptual-cognitive-motor learning method, comprising:
- displaying stereoscopic images of virtual objects moving in a three-dimensional environment on a display apparatus configured to provide to a subject a visual contact with the three-dimensional environment;
- defining a training sequence including a first plurality of successive tests, a second plurality of successive tests and a third plurality of successive tests, wherein the virtual objects move in the three-dimensional environment during the first, second and third plurality of successive tests;
- causing the display apparatus to present the virtual objects in accordance with the first plurality of successive tests to the subject;
- receiving, through a user interface, responses from the subject, the responses identifying the virtual objects during the first plurality of successive tests;
- receiving, through the user interface, commands from the subject, the commands consisting in at least one of:
  - causing the display apparatus to change a movement speed of the virtual objects;
  - causing the display apparatus to reset the movement of the virtual objects and;
  - setting a tracking speed of the virtual objects and presenting again the first plurality of successive tests to the subject, the movement speed of the virtual objects corresponding to the tracking speed;
- adding a first motor load to the subject during the second plurality of successive tests of the training sequence, the first motor load causing no efferent signal from the subject's brain;
- causing the display apparatus to present the virtual objects in accordance with the second plurality of successive tests to the subject,
- receiving, through the user interface, responses from the subject, the responses identifying the virtual objects during the second plurality of successive tests;
- adding a second motor load to the subject during the third plurality of successive tests of the training sequence, the second motor load being heavier than the first motor load;
- causing the display apparatus to present the virtual objects in accordance with the third plurality of successive tests to the subject,
- receiving, through the user interface, responses from the subject, the responses identifying the virtual objects during the third plurality of successive tests;
- adjusting the movement speed of the virtual objects in view of the responses received from the subject.

13. A method as defined in claim 12, further comprising changing the movement speed of the virtual objects in accordance with a staircase variation of speed.

14. A method as defined in claim 12, further comprising performing a preset number of tests using a shortened staircase variation of speed of the virtual objects after a pre-determined number of speed adjustments by the subject.

15. A method as defined in claim 12, wherein the user interface is selected from a group consisting of one or more buttons, a microphone, a motion capture device, a keyboard and a pedal board.

* * * * *